United States Patent
Escaich Ferrer et al.

(10) Patent No.: US 9,687,525 B2
(45) Date of Patent: *Jun. 27, 2017

(54) CARTILAGE PRODUCT

(71) Applicant: BIOIBERICA, S.A., Barcelona (ES)

(72) Inventors: Josep Escaich Ferrer, Barcelona (ES); Pere Dalmau Castanares, Palafolls (ES); Ana Maria Torrent Gibert, Fornells de la Selva (ES); Ramon Ruhi Roura, Barcelona (ES); Carlos Raul Alaez Verson, Blanes (ES)

(73) Assignee: BIOIBERICA, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/133,821

(22) Filed: Apr. 20, 2016

(65) Prior Publication Data

US 2016/0228508 A1    Aug. 11, 2016

Related U.S. Application Data

(63) Continuation of application No. 14/112,679, filed as application No. PCT/EP2012/056893 on Apr. 16, 2012, now Pat. No. 9,347,081.

(30) Foreign Application Priority Data

Apr. 19, 2011  (ES) .................................. 201130631
Sep. 21, 2011  (ES) .................................. 201131526

(51) Int. Cl.

| | | |
|---|---|---|
| *A61K 31/726* | (2006.01) | |
| *A61K 38/00* | (2006.01) | |
| *A61K 38/01* | (2006.01) | |
| *A61K 38/18* | (2006.01) | |
| *C12P 21/06* | (2006.01) | |
| *A61K 35/32* | (2015.01) | |
| *A61Q 19/08* | (2006.01) | |
| *A23L 1/305* | (2006.01) | |
| *A23J 1/00* | (2006.01) | |
| *A23J 3/34* | (2006.01) | |
| *A61K 8/66* | (2006.01) | |
| *A61K 8/73* | (2006.01) | |
| *A61K 8/65* | (2006.01) | |
| *A61K 38/39* | (2006.01) | |
| *A61Q 19/00* | (2006.01) | |
| *A23L 33/18* | (2016.01) | |
| *A61K 8/64* | (2006.01) | |
| *A61K 31/728* | (2006.01) | |
| *A61K 31/737* | (2006.01) | |

(52) U.S. Cl.
CPC ........... *A61K 38/1841* (2013.01); *A23J 1/002* (2013.01); *A23J 3/342* (2013.01); *A23L 1/3053* (2013.01); *A23L 33/18* (2016.08); *A61K 8/64* (2013.01); *A61K 8/65* (2013.01); *A61K 8/66* (2013.01); *A61K 8/73* (2013.01); *A61K 8/735* (2013.01); *A61K 31/728* (2013.01); *A61K 31/737* (2013.01); *A61K 35/32* (2013.01); *A61K 38/39* (2013.01); *A61Q 19/007* (2013.01); *A61Q 19/08* (2013.01); *C12P 21/06* (2013.01); *A23V 2002/00* (2013.01); *A61K 2800/592* (2013.01); *A61K 2800/5922* (2013.01); *A61K 2800/80* (2013.01)

(58) Field of Classification Search
None
See application file for complete search history.

(56) References Cited

U.S. PATENT DOCUMENTS

| | | |
|---|---|---|
| 3,400,199 A | 9/1968 | Balassa |
| 3,478,145 A | 11/1969 | Balass |
| 2003/0091652 A1 | 5/2003 | Ishaq et al. |
| 2007/0293427 A1 | 12/2007 | Vouland et al. |

FOREIGN PATENT DOCUMENTS

| | | |
|---|---|---|
| CN | 1134818 A | 11/1996 |
| ES | 8 605 285 A1 | 8/1986 |
| GB | 1041172 A | 9/1966 |
| WO | 96/14335 A1 | 5/1996 |
| WO | 97/16197 A1 | 5/1997 |
| WO | WO 97/16197 * | 5/1997 |
| WO | 2007122179 A1 | 11/2007 |

OTHER PUBLICATIONS

Spanish Search Report dated Jan. 25, 2013, 2 pages.
International Search Report, PCT/EP2012/056893, Date of Mailing: Jun. 8, 2012, 3 pages.

* cited by examiner

*Primary Examiner* — Elizabeth C Kemmerer
(74) *Attorney, Agent, or Firm* — Rothwell, Figg, Ernst & Manbeck, P.C.

(57) ABSTRACT

The present invention relates to a method for preparing a cartilage product comprising a protein hydrolysate with a degree of hydrolysis comprised between 0.5% and 3.0%, at least one glycosaminoglycan and at least one growth factor. The present invention also relates to the cartilage product obtainable through said method. Said cartilage product is useful in the treatment or prevention of wounds, ulcers, burns, psoriasis, osteoarthritis, synovitis, osteoporosis, osteopenia, diseases of the tendons and ligaments, periodontal diseases, signs of skin aging, the harmful effects of ultraviolet radiation exposure or stretch marks.

14 Claims, 6 Drawing Sheets

CARTILAGE PRODUCT

CROSS-REFERENCE TO RELATED APPLICATIONS

The present application is a continuation of U.S. patent application Ser. No. 14/112,679 filed on 9 Jan. 2014, now U.S. Pat. No. 9,347,081 which in turn is a national phase entry under 35 U.S.C. §371 of PCT/EP2012/056893, filed on 16 Apr. 2012, and claims the benefit of priority to Spanish Patent Application No. P 201131526, filed 21 Sep. 2011 and Spanish Patent Application No. P 201130631, filed 19 Apr. 2011. Each application is incorporated herein by reference in its entirety.

TECHNICAL FIELD OF THE INVENTION

The present invention relates to a method for preparing a cartilage product. The present invention also relates to the cartilage product obtainable through said method, as well as to the uses of thereof.

BACKGROUND OF THE INVENTION

The matrix metalloproteases (MMPs) and their endogenous regulators, the tissue inhibitors of MMPs (TIMPS) are responsible for the physiological remodeling of the extracellular matrix in healthy connective tissues. They are precisely regulated under normal physiological conditions, but when dysregulated they become a cause of many diseases such as chronic ulcers, osteoarthritis, rheumatoid arthritis, psoriasis, etc (A. L. Clutterbuck et al., *Curr. Drug Targets* 10(2), 1245-1254 (2009); I. Flisiak et al., *Przegl Lek.* 62(2), 119-122 (2005); H. Nagase et al., *Cardiovascular Research* 69, 562-573 (2006); X. Liu et al., *Muscle Nerve* 41(2), 174-178 (2010).

In view of the above, MMPs inhibitors are a potential treatment for wound healing, skin aging, psoriasis, osteoporosis, osteoarthritis, synovial inflammation, a periodontal disease and a muscle condition.

The healing process is a complex and dynamic process involving the coordinated participation of different cell types. During the first phase of healing, referred to as the inflammatory phase, platelets, neutrophils, granulocytes and macrophages play a key role in the transition between inflammation and repair by means of the release of growth factors. Growth factors released by monocytes and macrophages are necessary for starting and propagating new tissue that will cover wounds (A. J. Singer et al., *N. Engl. J. Med.* 341, 738-746 (1999)). During this phase, degenerated tissue is eliminated, which is a pre-requisite for optimal healing. The second phase of wound healing, referred to as the regenerative phase, is characterized by cell proliferation and extracellular matrix synthesis. In this stage of the healing process, highly vascularized tissue is formed, and several cell types, including macrophages, fibroblasts, angioblasts and myofibroblasts travel to the site of the injury. Macrophages providing a continuous source of growth factors, fibroblasts proliferate and synthesize a new extracellular matrix, which leads to the rapid formation of tissue of granulation, endothelial cells generate an angiogenesis or new vessel formation process which is stimulated by growth factors (VEGF and FGF) released by macrophages, but also by fibroblasts. In addition to angiogenic factors, the presence of a suitable extracellular matrix formed by fibronectin, and the presence of endothelial receptors which recognize this extracellular matrix are also necessary. During the final phase of the process, referred to as remodeling phase, the major cellular phenomena are the production of new connective tissue formed mainly by fibroblasts and keratinocyte proliferation and migration leading to wound re-epithelialization.

As soon as the fibroblasts synthesize collagen fibers of the new extracellular matrix, mitotic activity is reduced, as is cell density and tissue vascularization. Both collagen deposition and fibroblast orientation are determined by fibronectin, which is the most important protein of the extracellular matrix in this phase of the process (D. Greiling et al., *J. Cell. Sci.* 110, 861-870 (1997)). Physiological re-epithelialization is started by several stimuli: growth factors; the absence of neighboring cells at the edges of the wound, which triggers both the proliferation and migration of epidermal cells; the loss of contact of the epidermal cells with the baseline membrane, and the establishment of new interactions between cells with the components of the dermal matrix; the production and release of collagenase or MMP1 by epidermal cells and the activation of plasmin by plasminogen, which in turn activates collagenase (Fini et al., *Am. J. Pathol.* 149, 1287-1302 (1996)).

There are two types of skin aging, intrinsic or chronological aging and extrinsic aging, which is mostly linked to exposure to the sun (L. Rittié et al., *Ageing Res. Rev.* 1, 705-720 (2002)).

The intrinsic aging, also known as the natural aging process, is a continuous process that usually begins after 25 years.

For women, aging due to the reduction of estrogen production in menopause is added to the chronological process.

The firmness, elasticity and moisturizing of the skin are fundamentally consequences of the extracellular matrix of the dermis which is secreted by the cellular elements thereof, the fibroblasts, and mainly consists of type I and III collagen, responsible for its firmness and structuring, elastin, which confers the elastic properties thereof, and hyaluronic acid, the major glycosaminoglycan necessary for maintenance of moisturizing levels. Skin thickness is a consequence of both extracellular and cellular elements. The greater skin thickness, the larger the number of cells and the greater the amount of elements of the extracellular matrix there are (G. Jenkins, *Mech. of Ageing Dev.* 123, 801-810 (2002)).

A skin anti-aging cosmetic composition is one which is on one hand invigorating, restructuring and moisturizing, and on the other hand reduces the effects that age causes in the skin, modifying its appearance both in terms of texture and roughness.

An important anti-aging action is achieved when skin cells respond to the cosmetic composition, prolonging their life cycle, delaying the manifestation of the symptoms of cellular aging, such as the limitation of growth, the production of extracellular proteins, the increase in size or keratinization.

Another crucial property of an anti-aging product is that it should be capable of reducing the signs of age when they are already present in the skin.

Psoriasis is a disease that affects the skin. It presents a great clinical polymorphism (M A Johnson et al, *Clin. Rev. Allergy. Immunol.*, January 27 (2012)). The skin lesion clinically manifests in the form of an erythematous plaque with well-defined edges covered by thick, whitish squamae with a waxy appearance distributed preferably by areas of extension. It is characterized by epidermal keratinocyte proliferation and failure of maturation of these cells in normal keratin formation. The evolution of the disease is unpredictable and it has been shown to greatly affect the quality of life of the patient (M M Heller et al, *Dermatol. Clin.* 30 (2), 281-291 (2012)).

Psoriasis is a chronic disease that has no definitive treatment. Current medical treatment depends on the type of lesion, location and age of the patient (I A Al-Hogail, *Curr Vasc Pharmacol* 8 (3), 432-436 (2010)).

Osteoarthritis (arthrosis), is a degenerative joint disease affecting most people after 65 years of age, and is characterized by a gradual degradation of the cartilaginous tissue, combined with the presence of inflammation and pain. Synovial inflammation usually appears later on when the disease is in its advanced stage, and it is generally only a secondary component in the pathology of osteoarthritis.

Osteoarthritis can be defined as degeneration of the hyaline articular cartilage. A secondary effect thereto is the damage of the synovial membrane and the subchondral bone (bone in contact with the cartilage), as well as new bone formation at the edges of joint surfaces.

Cartilage allows bones to move by sliding over one another. It also absorbs the tension caused by physical movement. In osteoarthritis, the surface of the cartilage breaks and wears down, causing bones to move against one another, causing friction, pain, swelling and loss of movement in the joint. The joint can become deformed over time.

Under normal conditions, cartilage renewal is a very slow process consisting of constant synthesis (anabolism) and degradation (catabolism) of the components of the extracellular matrix. Chondrocytes are the cells responsible for this metabolism, a process that must be perfectly coordinated.

Although the etiology of osteoarthritis is still unknown, it is currently accepted to be true that the first alterations occur at the chondrocyte level, which alterations will subsequently lead to the onset of an osteoarthritic joint.

A series of risk factors for the onset of the disease have been described, including: aging, genetics, obesity, overburden-induced disorders, decrease in sexual hormones, excess physical exertion in athletes, injuries or traumas, work activity and low bone mineral density.

Osteoarthritis is a disease that has no definitive treatment. There is a great need to develop disease-modifying agents to improve the quality of life of those suffering the disease, as well as to reduce the healthcare costs it entails (N. Schmitz et al., *Curr. Drug Targets* 11 (5), 521-527 (2010)).

Osteoporosis is a disease characterized by low bone mass and structural deterioration of bone tissue, which entails an increase in bone fragility and to a greater risk of fractures and microfractures. The most common fractures are in the hip, spinal column and wrist. It is a disease that often develops asymptomatically, so it is not detected until there is a fracture.

Bones constantly perform metabolic turnover by means of a combination of osteoblasts-induced bone formation and osteoclast-induced bone resorption. The alteration of bone metabolism can be characterized by a bone formation and bone resorption imbalance. A process of loss of bone mass begins after the age of 40 years in both sexes which is accentuated in menopausal women. With the decrease in estrogens levels, bone resorption increases and causes a negative effect on bone density.

Hip fractures are a serious result of osteoporosis. These fractures cause considerable chronic pain, disability and loss of independence, which entails a high cost for health services.

On the other hand, osteopenia is characterized by a decrease in bone mineral density which can be a precursor to osteoporosis. However, not just any person diagnosed with osteopenia will develop osteoporosis. Bone mineral density (BMD) is measured to diagnose osteopenia and osteoporosis.

Cartilage is a type of flexible connective tissue covering the joints and providing structure to the nose, ears, larynx, trachea and other parts of the body. It is a tissue without blood vessels, nerves or lymphatic vessels. Cartilaginous fish, also called elasmobranchs, such as sharks and rays, have a cartilage skeleton.

Three types of cartilaginous tissue have been described, the hyaline cartilage, fibrous cartilage and elastic cartilage. Hyaline cartilage is the most important type in the body, being found in the nose, larynx, trachea, bronchia, costal margins and articular ends of the bones.

Cartilage is formed by 70%-80% water. The main substances additionally forming cartilage are: chondrocytes, collagen, proteoglycans and hyaluronic acid. Proteoglycans mostly contain chondroitin sulfate and keratan sulfate (D. W. Fawcett, 1995, Tratado de Histologia, Ed. Interamericana McGraw-Hill, $12^{th}$ Edition, Madrid; D. W. Fawcett, 1986, Textbook of Histology, Ed. Chapman and Hall, $12^{th}$ Edition, New York, London; T. Aigner et al., *Advanced Drug Delivery Reviews* 55, 1569-1593 (2003)).

Collagen is a complex structural protein. There are several types of collagen. In cartilage, the most abundant collagen is type II. All collagens are formed by three polypeptide chains which are twisted and joined together by means of transverse bonds to form a triple helix.

Glycosaminoglycans (GAG) are high molecular weight polymeric biomolecules consisting of a repeated dimeric structure. They are fundamentally found in living organisms where they perform different physiological functions. The major glycosaminoglycan in cartilage is chondroitin sulfate which has a polymeric structure characterized by a repeating disaccharide, formed by N-acetyl-D-galactosamine and D-glucuronic acid. Most N-acetyl-D-galactosamine residues are sulfated. Chondroitin sulfate is a fundamental component of cartilage proteoglycans.

Another glycosaminoglycan that is found in cartilage is hyaluronic acid. It is a non-sulfated glycosaminoglycan with a polymeric structure characterized by a repeating disaccharide, formed by the monosaccharides N-acetyl-D-glucosamine and D-glucuronic acid.

Growth factors are substances, most being of a proteinaceous nature, which carry out an important function in intercellular communication. They are capable of stimulating cell growth and differentiation, thus regulating a wide variety of cellular processes. In the human body they carry out their function at a very low concentration, in the order of the picograms.

The use of collagen preparations for the controlled release of active substances in a wound has been described (U.S. Pat. No. 6,761,908).

EP 154447 describes a composition for wound healing consisting of an aqueous suspension of collagen and a glycosaminoglycan. While collagen-heparin and collagen-alginate compositions present good activity, the inventor stresses that collagen-chondroitin sulfate and collagen-hyaluronate preparations are less useful in the treatment of wounds.

Some methods for producing cartilage preparations are described in the literature, but they differ from the method used in the present invention and, therefore, result in cartilage products that are also different:

U.S. Pat. No. 5,503,990 describes a method for preparing finely divided bovine trachea cartilage of uniform size. This method uses enzymatic treatment to remove the unwanted protein. The cartilage that is obtained is sparingly water-soluble.

U.S. Pat. No. 3,400,199 describes a method for preparing a cartilage powder for treating wounds, with a particle size less than 40 microns and with an average particle size comprised between 5 and 10 microns. This method uses enzymatic treatment with acid-pepsin during only six hours for the purpose of removing tissue adhered to cartilage. The cartilage powder that is obtained is sparingly water-soluble.

In view of the foregoing, it is of great interest to find a method for preparing a new cartilage product containing growth factors of a natural origin at concentrations not exceeding physiological concentrations, which is water-soluble and can be useful in the treatment or prevention of wounds, signs of skin aging, psoriasis, osteoarthritis, periodontitis, muscular atrophy or osteoporosis.

DISCLOSURE OF THE INVENTION

The authors of the present invention have surprisingly found that the method of the present invention allows obtaining a cartilage product containing growth factors of a natural origin at concentrations not exceeding physiological concentrations, that is water-soluble, organic-solvent free, does not contain added inorganic sodium and contains a large amount of protein hydrolysate with a degree of hydrolysis comprised between 0.5% and 3.0% and of chondroitin sulfate.

Furthermore, the cartilage product has an important inductive effect on human dermal fibroblast proliferation, an inductive effect on human dermal fibroblast migration, an inductive effect on hyaluronic acid production in human dermal fibroblasts, which translates into a moisturizing action, an inductive effect on skin elasticity, an inhibitory effect on metalloprotease activity and an inhibitory effect on muscular atrophy. Furthermore, the cartilage product does not present cellular toxicity, is stable, improves the healing quality of wounds, is effective in the treatment of psoriasis, inhibiting the IL-17 levels, reduces cartilage degradation, increases bone volume, increases trabecular number and increases bone surface density. Therefore, the cartilage product of the present invention can be used in the treatment of wounds and/or ulcers and/or burns, for treating, delaying or preventing the signs of skin aging and in the treatment or prevention of psoriasis, osteoarthritis or osteoporosis.

Therefore, the present invention describes a method for preparing a cartilage product comprising the following steps:
 a) chopping the cartilage;
 b) mixing the chopped cartilage and water;
 c) heating the mixture of step b) at a temperature of less than 60° C.;
 d) adding an aqueous solution of $H_3PO_4$ to adjust the pH of the mixture of step c) to a value comprised between 1.5 and 4.5;
 e) treating the acid mixture of step d) with an amount of pepsin by weight with respect to the weight of the cartilage of step a) comprised between 0.6% and 4.6% for a period of time comprised between 10 and 30 hours, such that a solution is obtained;
 f) neutralizing the solution of step e) with $Ca(OH)_2$, and
 g) filtering the solution of step f) containing insoluble salts, such that an aqueous solution of the cartilage product is obtained, wherein the cartilage product comprises a protein hydrolysate with a degree of hydrolysis comprised between 0.5% and 3.0%, at least one glycosaminoglycan and at least one growth factor.

Preferably, the degree of hydrolysis is 1.7%.

In a preferred embodiment, the method comprises an additional step after step g), in which a solid cartilage product is obtained from the aqueous solution of step g). Preferably, the solid cartilage product is obtained by atomization.

In another, equally preferred embodiment, in step e) the amount of pepsin by weight with respect to the weight of the cartilage of step a) is comprised between 0.6% and 1.0%, in step d) the pH value is comprised between 3.0 and 3.5, and in step c) the temperature is comprised between 45° C. and 55° C. Preferably, in step e) the amount of pepsin by weight with respect to the weight of the cartilage of step a) is comprised between 0.7% and 0.8%, in step e) the period of time is comprised between 20 and 28 hours and in step c) the temperature is 50° C. More preferably, in step e) the amount of pepsin by weight with respect to the weight of the cartilage of step a) is 0.75% and the time is 24 hours.

In another, equally preferred embodiment, step f) of neutralization is performed after (i) heating the solution of step e) for one hour at a temperature comprised between 75° C. and 90° C., such as 80° C. for example; (ii) filtering, and (iii) bleaching.

The bleaching can be performed with activated carbon at a temperature of, for example, 50° C., and during a time of, for example, 30 minutes.

In another, equally preferred embodiment, the method comprises an additional step before step a), in which the cartilage is subjected to mechanical cleaning to remove fat and non-cartilaginous tissues.

In another, equally preferred embodiment, in step e) the pepsin is added in a fractionated manner, with pH adjustments. For example, the total amount of pepsin can be divided into two or three fractions, and the pH can be checked and if necessary adjusted every hour or every 30 minutes.

Preferably, the pepsin has an activity of 1:3000 FCC, where FCC is the abbreviation for "Food Chemical Codex". For example, pepsin of Biocatalysts, 1:3000 MDP, can be used.

In another, equally preferred embodiment, the cartilage product further comprises at least one protein of the serpin family.

In the present invention, the term "chopping the cartilage" relates to reducing the size of the pieces of cartilage to, for example, a size comprised between 2 mm and 30 mm.

Preferably, the cartilage is mammalian tracheal cartilage, avian sternal cartilage or elasmobranch fish cartilage. The mammalian trachea is selected from porcine, bovine or camel trachea. The elasmobranch fish is selected from shark and ray. More preferably, the cartilage is porcine tracheal cartilage.

The present invention also relates to a cartilage product obtainable by the method defined above.

Preferably, the glycosaminoglycan is selected from the group consisting of chondroitin sulfate, hyaluronic acid, keratan sulfate and mixtures thereof, and the growth factor is selected from the group consisting of TGF-β1, TGF-β3 and mixtures thereof.

Chondroitin sulfate has a polymeric structure characterized by a repeating disaccharide, formed by N-acetyl-D-galactosamine and D-glucuronic acid. The chondroitin sulfate from cartilaginous tissue is mainly found in two isomeric forms differing in position of the sulfate group present in the residue of N-acetylgalactosamine, 4-chondroitin sulfate (chondroitin sulfate A) and 6-chondroitin sulfate (chondroitin sulfate C).

Hyaluronic acid is a non-sulfated glycosaminoglycan with a molecular weight comprised between 100,000 daltons and 3,000,000 daltons. Its polymeric structure is characterized by a repeating disaccharide, formed by N-acetyl-D-glucosamine and D-glucuronic acid.

The keratan sulfate from cartilaginous tissue has a polymeric structure characterized by a repeating disaccharide, formed by D-galactose and N-acetyl-D-glucosamine. The sulfate groups are for the most part incorporated in C6 positions of the N-acetyl-D-glucosamine residues and/or in C6 positions of the D-galactose residues.

The growth factors are present in the cartilage product of the present invention at a very low concentration, in the order of picograms for every 100 mg of anhydrous cartilage product.

Therefore, the method of the present invention allows obtaining a cartilage product with a concentration of growth factors not exceeding the physiological concentration.

ELISA kits (R&D Systems) can be used to determine the growth factors of the cartilage product of the present invention following the protocols recommended by the manufacturer.

In a preferred embodiment, the cartilage product comprises:

a) between 67% and 87% by weight of protein hydrolysate with a degree of hydrolysis comprised between 0.5% and 3.0%, with respect to the weight of the anhydrous cartilage product;

b) between 15% and 25% by weight of chondroitin sulfate, with respect to the weight of the anhydrous cartilage product;

c) between 0.1% and 1.0% by weight of hyaluronic acid, with respect to the weight of the anhydrous cartilage product;

d) between 20 pg and 200 pg of TGF-β1 for every 100 mg of anhydrous cartilage product, and e) between 20 pg and 200 pg of TGF-β3 for every 100 mg of anhydrous cartilage product.

For example, the cartilage product comprises:

a) 77% by weight of protein hydrolysate with a degree of hydrolysis of the 1.7%, with respect to the weight of the anhydrous cartilage product;

b) 19.7% by weight of chondroitin sulfate, with respect to the weight of the anhydrous cartilage product;

c) 0.3% by weight of hyaluronic acid, with respect to the weight of the anhydrous cartilage product;

d) 53.0 pg of TGF-β1 for every 100 mg of anhydrous cartilage product, and e) 31.3 pg of TGF-β3 for every 100 mg of anhydrous cartilage product.

The protein hydrolysate is mostly formed by collagen hydrolysate with a degree of hydrolysis less than 3.0%.

In another, equally preferred embodiment, the cartilage product comprises between 45% and 65% by weight of collagen hydrolysate with a degree of hydrolysis less than 3.0%, with respect to the weight of the anhydrous cartilage product. For example, the cartilage product comprises 54.9% by weight of collagen hydrolysate with a degree of hydrolysis less than 3.0%, with respect to the weight of the anhydrous cartilage product. Preferably, the collagen hydrolysate has a degree of hydrolysis of, for example, 0.1%, 0.2%, 1.0% or 2.0%, more preferably of 0.1%. Also preferably, the collagen hydrolysate is type II collagen hydrolysate.

In another, equally preferred embodiment, the cartilage product has the following analytical parameters:

Degree of hydrolysis of the protein: comprised between 0.5% and 3.0%;

Degree of hydrolysis of the collagen hydrolysate: less than 3%;

Protein hydrolysate: between 67% and 87% by weight with respect to the weight of the anhydrous cartilage product;

Collagen hydrolysate: between 45% and 65% by weight with respect to the weight of the anhydrous cartilage product;

Chondroitin sulfate: between 15% and 25% by weight with respect to the weight of the anhydrous cartilage product;

Hyaluronic acid: between 0.1% and 1.0% by weight with respect to the weight of the anhydrous cartilage product;

Growth factor TGF-β1: between 20 pg and 200 pg for every 100 mg of anhydrous cartilage product;

Growth factor TGF-β3: between 20 pg and 200 pg for every 100 mg of anhydrous cartilage product.

In another, equally preferred embodiment, the cartilage product has the following analytical parameters:

Degree of hydrolysis of the protein: 1.7%;

Degree of hydrolysis of the collagen hydrolysate: 0.1%;

Protein hydrolysate: 77% by weight with respect to the weight of the anhydrous cartilage product;

Collagen hydrolysate: 54.9% by weight with respect to the weight of the anhydrous cartilage product;

Total amino acids: 70.7% by weight with respect to the weight of the cartilage product;

Free amino acids: 1.2% by weight with respect to the weight of the cartilage product;

Chondroitin sulfate: 19.7% by weight with respect to the weight of the anhydrous cartilage product;

Hyaluronic acid: 0.3% by weight with respect to the weight of the anhydrous cartilage product;

Growth factor TGF-β1: 53.0 pg for every 100 mg of anhydrous cartilage product;

Growth factor TGF-β3: 31.3 pg for every 100 mg of anhydrous cartilage product;

Calcium: 0.4% by weight with respect to the weight of the anhydrous cartilage product;

Phosphates: 0.3% by weight with respect to the weight of the anhydrous cartilage product.

The present invention also relates to a cartilage product characterized by the following analytical parameters:

Degree of hydrolysis of the protein: comprised between 0.5% and 3.0%;

Degree of hydrolysis of the collagen hydrolysate: less than 3%;

Protein hydrolysate: between 67% and 87% by weight with respect to the weight of the anhydrous cartilage product;

Collagen hydrolysate: between 45% and 65% by weight with respect to the weight of the anhydrous cartilage product;

Chondroitin sulfate: between 15% and 25% by weight with respect to the weight of the anhydrous cartilage product;

Hyaluronic acid: between 0.1% and 1.0% by weight with respect to the weight of the anhydrous cartilage product;

Growth factor TGF-β1: between 20 pg and 200 pg for every 100 mg of anhydrous cartilage product;

Growth factor TGF-β3: between 20 pg and 200 pg for every 100 mg of anhydrous cartilage product.

The present invention also relates to a food supplement comprising the cartilage product defined above, and at least one nutritional excipient. Likewise, the present invention relates to a functional food comprising the cartilage product defined above and at least one nutritional excipient.

The present invention also relates to a cosmetic composition comprising the cartilage product defined above and at least one cosmetically acceptable excipient.

Likewise, the present invention also relates to a pharmaceutical composition comprising the cartilage product defined above and at least one pharmaceutically acceptable excipient.

In another preferred embodiment, the food supplement, the functional food or the pharmaceutical composition further comprises a calcium salt and optionally a vitamin D and/or a vitamin K.

The calcium salt can be calcium carbonate, calcium phosphate, calcium lactate, calcium glycerophosphate, calcium lactogluconate or hydroxyapatite. Preferably it is hydroxyapatite.

The most preferred vitamin D is vitamin D3.

The vitamin K can be vitamin K1 or vitamin K2. Preferably it is vitamin K2.

In another preferred embodiment, the food supplement, the functional food or the pharmaceutical composition further comprises a magnesium salt.

The present invention also relates to a cartilage product defined above for use as a medicament.

Likewise, the present invention also relates to a cartilage product defined above for its use in the treatment or prevention of a disorder or disease mediated by a metalloprotease, wherein the disorder or disease is selected from a wound, an ulcer, a burn, psoriasis, osteoarthritis, synovitis, osteoporosis, osteopenia, a bone fracture, a disease or injury of a tendon, a disease or injury of a ligament, a periodontal disease, the signs of skin aging and a muscle condition.

Likewise, the present invention also relates to a cartilage product defined above for its use in the treatment or prevention of a wound, an ulcer, a burn, psoriasis, osteoarthritis, synovitis, osteoporosis, osteopenia, a bone fracture, a disease or injury of a tendon, a disease or injury of a ligament, a periodontal disease, the signs of skin aging or a muscle condition.

Preferably, the periodontal disease is periodontitis.

Preferably, the muscle condition is selected from the group consisting of aching muscle, torn muscle, muscle loss, muscle weakness, sarcopenia, muscular atrophy and muscle fatigue, more preferably muscular atrophy.

Likewise, the present invention also relates to a food supplement or to a functional food defined above for use in preventing the formation of a wound or ulcer, in improving the healing quality of a wound, an ulcer or burn, in preventing or reversing a psoriatic lesion, in preventing osteoarthritis, in nourishing the joint, in preventing, stabilizing or repairing an injury or defect of cartilage, the synovial membrane or the subchondral bone, in increasing joint mobility, in reducing synovitis, in preventing osteoporosis or osteopenia, in increasing bone mass density, in repairing bone fractures, in increasing calcium absorption, in preventing or repairing an injury of a tendon or ligament, in preventing or reversing a periodontal condition or muscle condition, in delaying, decreasing or preventing the signs of skin aging or as a chondroprotector.

The present invention also relates to the use of a cartilage product defined above for the preparation of a medicament for the treatment or prevention of a wound, an ulcer, a burn, psoriasis, osteoarthritis, synovitis, osteoporosis, osteopenia, a bone fracture, a disease or injury of a tendon, a disease or injury of a ligament, a periodontal disease or a muscle condition, more preferably, a wound, an ulcer, osteoarthritis or osteoporosis.

In another preferred embodiment, the treatment or prevention of osteoarthritis and osteoporosis is simultaneous.

The present invention also relates to the use of a cosmetic composition defined above for treating, delaying, decreasing or preventing the signs of skin aging, the harmful effects of ultraviolet radiation exposure or stretch marks.

The present invention also relates to the use of a cartilage product defined above for the preparation of a food supplement or of a functional food for preventing the formation of a wound or ulcer, improving the healing quality of a wound, an ulcer or burn, preventing or reversing a psoriatic lesion, preventing the osteoarthritis, nourishing the joint, preventing, stabilizing or repairing an injury or defect of cartilage, the synovial membrane or the subchondral bone, increasing joint mobility, reducing synovitis, preventing osteoporosis or osteopenia, increasing bone mass density, repairing bone fractures, increasing calcium absorption, preventing or repairing an injury of a tendon or ligament, preventing or reversing a periodontal condition or muscle condition, delaying, decreasing or preventing the signs of skin aging or as a chondroprotector.

Since the method for preparing the cartilage product includes enzymatic digestion and the raw material is of an animal origin, the analytical characteristics of the cartilage product obtained can slightly vary depending on the production batch.

The protein contained in the cartilage product of the present invention has a degree of hydrolysis comprised between 0.5% and 3.0%, such as for example 1.7%.

In methods described in the literature, cartilage products are obtained with degrees of hydrolysis of the protein less than those of the present invention or much greater.

The degree of hydrolysis of the protein can be determined by means of a standard method, being expressed as the percentage of free amino acids in relation to total amino acids.

The degree of hydrolysis of the collagen hydrolysate can be determined by means of a standard method, being expressed as the percentage of free hydroxyproline in relation to total hydroxyproline.

In the methods of preparing cartilage products described in the literature, it is common to include a step in which the product is treated with an organic solvent, such as acetone or hexane, to remove the fat (see U.S. Pat. Nos. 3,400,199 and 5,503,990), The method of the invention has the advantage of not using organic solvents, which allows obtaining a cartilage product without traces of said solvents.

In the methods of the literature in which a partially water-soluble cartilage product is obtained, part of the protein hydrolysate and of the glycosaminoglycans is lost during the washing process.

In the method of the present invention, the conditions of enzymatic digestion of step e) allow, on one hand, obtaining a cartilage product with growth factors of a natural origin, and on the other hand obtaining an aqueous solution of the cartilage product, preventing losses of protein hydrolysate, glycosaminoglycans and growth factors.

The authors of the present invention have found that the following variables: type of enzyme, concentration of enzyme, temperature, pH value, time of enzymatic digestion, type of solvent, type of acid and type of base, are key to obtaining a specific cartilage product.

In the present invention it has been found that by using pepsin for the enzymatic digestion, in an amount by weight with respect to the initial weight of cartilage, comprised between 0.6% and 4.6%, during a time comprised between 10 and 30 hours, at a temperature of less than 60° C., and at a pH comprised between 1.5 and 4.5, and by using $H_3PO_4$ as the acid, $Ca(OH)_2$ as the base and water as the solvent in the method, a new cartilage product having the following advantages is obtained: (i) it contains growth factors of a natural origin at a concentration not exceeding the physiological concentration, (ii) it is completely water-soluble, (iii) it is free of organic solvents, (iv) it does not contain added inorganic sodium, (v) it contains a high amount of protein hydrolysate with a degree of hydrolysis comprised between 0.5% and 3.0%, (vi) it contains a high amount of chondroitin sulfate, (vii) it is not is toxic, (viii) it is stable, (ix) it induces human dermal fibroblast proliferation, (x) it induces human dermal fibroblast migration, (xi) it induces hyaluronic acid production in human dermal fibroblasts, which translates into moisturizing action, (xii) it induces elastin production, (xiii) it has an inhibitory effect on metalloprotease activity, (xiv) it improves the healing quality of wounds, (xv) it inhibits muscular atrophy, (xvi) it is effective in the treatment of psoriasis, inhibiting IL-17 levels, (xvii) it reduces cartilage degradation, (xviii) it increases bone volume, (xix) it increases the trabecular number and (xx) it increases bone surface density.

Furthermore, the cartilage product of the present invention does not contain native collagen.

The authors of the present invention have found that when they change the conditions of the method of preparation, the cartilage product obtained is different from that obtained according to the method of the present invention. Therefore, when 0.35% of pepsin is used and digestion is performed for only six hours, a cartilage product in which free amino acids are not detected is obtained, so the degree of hydrolysis can be considered insignificant. In addition, when the same method of the present invention is followed but 10% of pepsin is used, the cartilage product which is obtained has a higher degree of hydrolysis of the protein, more specifically 5.2%, instead of the degree of hydrolysis of between 0.5% and 3.0% which the cartilage product of the present invention has.

The following abbreviations have been used in the present invention:

TGF-β1 for transforming growth factor beta 1
TGF-β3 for transforming growth factor beta 3
BV for bone volume ($mm^3$)
BS for bone surface ($mm^2$)
TV for total volume ($mm^3$)
Tb·Th for trabecular thickness (mm)
BV/TV(%) for bone volume/total tissue volume=% of bone volume.
BS/TV for bone surface/total tissue volume=bone surface density ($mm^{-1}$).
Tb·N for trabecular number ($mm^{-1}$); (Tb·N=BV/TV× Tb·Th).

When referring to signs of skin aging in the present invention, reference is made primarily to wrinkles, expression lines, flaccidity, dry skin and dull skin.

To use the cartilage product of the present invention in the treatment or prevention of a wound, an ulcer, a burn, psoriasis, osteoarthritis, synovitis, osteoporosis, osteopenia, a bone fracture, a disease or injury of a tendon, a disease or injury of a ligament, a periodontal disease, the signs of skin aging or a muscle condition, is formulated in suitable pharmaceutical compositions, using conventional techniques and excipients or carriers, such as those described in *Remington: The Science and Practice of Pharmacy* 2000, edited by Lippincott Williams and Wilkins, 20th edition, Philadelphia. The pharmaceutical compositions comprise the cartilage product and at least one pharmaceutically acceptable excipient for administration to the patient. Said pharmaceutical compositions can be administered to the patient at required doses. The administration of the pharmaceutical compositions can be done through different routes, for example, topical, oral, intravenous, intralesional, perilesional, intratendinous, peritendinous, subcutaneous, intramuscular, sublingual, transdermal or intranasal. The pharmaceutical compositions of the invention include a therapeutically effective amount of the cartilage product, said amount depending on many factors, such as for example, the physical condition of the patient, age, sex, administration route, administration frequency or seriousness of the disease. It will further be understood that said dosage of cartilage product can be administered in single or multiple dose units to provide the desired therapeutic effects.

The pharmaceutical preparations of the invention will generally be in solid, liquid or the form of a gel. Pharmaceutical preparations in solid form that can be prepared according to the present invention include powders, pellets, microspheres, nanoparticles, tablets, dispersible granules, capsules, cachets and suppositories. Preparations in liquid form include solutions, suspensions, emulsions, syrups and elixirs. Preparations of solid forms to be converted immediately before being used into preparations in liquid form are also contemplated. Said liquid forms include solutions, suspensions and emulsions.

Preferably, the pharmaceutical preparations for the treatment of wounds or ulcers by topical route will be in the form of a gel, powders or in any form presenting high viscosity to retain the pharmaceutical composition in the wound. Once the pharmaceutical composition is deposited in the wound, the latter can be covered with sterile gauze and/or a bandage. Dressings or patches containing the cartilage product and a solid support or membranes impregnated with the cartilage product can also be prepared.

To use the cartilage product of the present invention in the field of engineering bone or cartilaginous tissues, for example in the treatment of a bone or cartilage defect or injury, preparing hydrogels, injectable cements or three-dimensional matrices (scaffolds) containing the cartilage product is contemplated. The three-dimensional matrices can be prepared with the cartilage product itself or with a biodegradable material, such as for example polyglycolic acid, polylactic acid, cellulose, gelatin, collagen, collagen-hydroxyapatite, hydroxyapatite, pectin, alginate, dextran, hyaluronic acid or derivatives thereof. Matrices formed by non-biodegradable materials such as Teflon, polystyrene, polyacrylate or polyvinyl can also be used. The matrix can be flexible or rigid. The sponge-type structure can also be used.

To prepare both a food supplement and a functional food, the cartilage product is formulated with suitable components and/or excipients used in nutrition. The food supplement can be in the form of tablets, capsules, solutions, suspensions or sachets. The functional food can be in the form of yogurts, milk, fermented milk, fruit juices, vegetable juices, soups, dehydrated foods, cookies or baby foods.

When the cartilage product of the present invention is used for treating, delaying, decreasing or preventing the signs of skin aging, stretch marks or the harmful effects of ultraviolet radiation exposure or pollution, it is formulated in suitable cosmetic compositions, using techniques and excipients or carriers of known use in cosmetics and dermatology. The cosmetic composition can contain in addition to the cartilage product of the present invention, any plant extract, for example and not intending to be limiting, algae, rosemary or fruit extract, and one or several excipients and additives of known use in cosmetic and dermatological compositions, such as, for example and not intending to be limiting, perfumes, conditioners, dyes, surfactants, vitamins, preservatives, emulsifiers, emollients, oils, UV filters, glycols, etc. . . . . . The cosmetic compositions of the present invention can be presented under any form known by a person skilled in the art of cosmetics and dermatology, for example, in the form of cream, oil, emulsion, microemulsion, ointment, gel, foam, paste, lotion, poultice, spray or milk. Said cosmetic compositions can be applied on the face, body or hair.

DETAILED DESCRIPTION OF THE PREFERRED EMBODIMENTS

EXAMPLES

Figure 1:
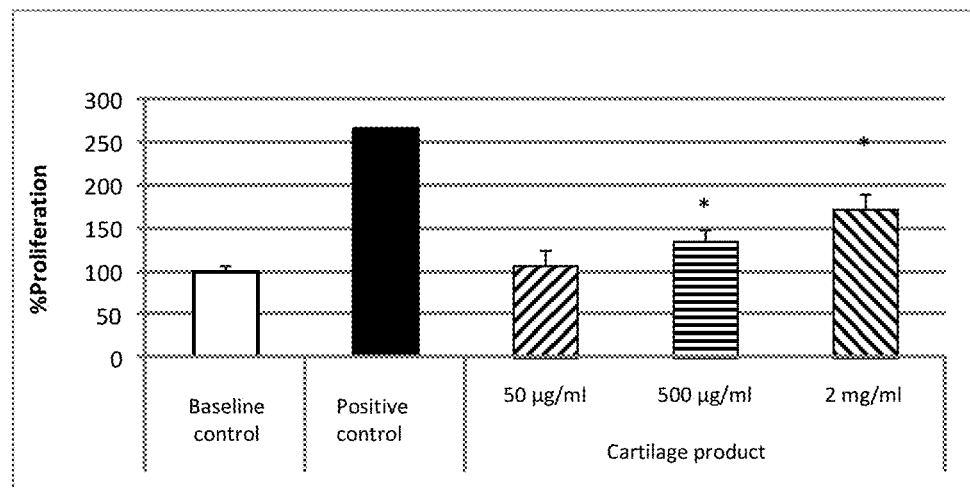
FIG. 1 shows the effect of the cartilage product on the percentage of human dermal fibroblast proliferation at 48 hours at three concentrations (50 µg/ml, 500 µg/ml and 2 mg/ml). The positive control (human dermal fibroblast culture in 10% FCS medium, in the absence of the cartilage product and in the presence of bromodeoxyuridine) and the baseline control (human dermal fibroblast culture in culture medium and in the absence of the cartilage product) are also included.

The following examples are merely illustrative and do not represent a limitation to the scope of the present invention.

Example 1

Preparation of a Porcine Tracheal Cartilage Product of the Invention

Pieces of porcine trachea were subjected to mechanical cleaning to remove fat and non-cartilaginous tissues and were then chopped up. 3,100 ml of deionized water were introduced in a reactor. 1,575 g of chopped porcine tracheal cartilage were added. The mixture was heated to 50° C. and the pH was adjusted between 3.0 and 3.5 with $H_3PO_4$. Once the pH was adjusted, 5.9 g of pepsin (Biocatalysts, 1:3000 MDP) were added and the temperature was maintained at 50° C. The pH was checked every 30 minutes for the next three hours and was adjusted if needed. Ten hours after starting digestion 5.9 g of pepsin (Biocatalysts, 1:3000 MDP) were again added and the pH was checked every 30 minutes for the next three hours. Digestion was performed for a total of 24 hours, a total amount of 0.75% of pepsin by weight with respect to the weight of the porcine tracheal cartilage being used. After 24 hours, it was heated to 80° C. for one hour. Then it was filtered to clarify the product. Once filtered, 7.9 g of activated carbon were added and it was heated to 50° C. for 30 minutes. It was neutralized with calcium hydroxide. It was then filtered, obtaining an aqueous solution of cartilage product. The end product in solid form (cream-colored powder) was obtained by atomizing the aqueous solution of cartilage product.

Analytical characteristics of the solid cartilage product obtained:

Protein hydrolysate: 77% by weight with respect to the weight of the anhydrous cartilage product;

Collagen hydrolysate: 54.9% by weight with respect to the weight of the anhydrous cartilage product;

Total amino acids: 70.7% by weight with respect to the weight of the cartilage product;

Free amino acids: 1.2% by weight with respect to the weight of the cartilage product;

Total hydroxyproline: 6.9% by weight with respect to the weight of the cartilage product;

Degree of hydrolysis of the protein: 1.7%;

Degree of hydrolysis of the collagen hydrolysate: 0.1%;

Chondroitin sulfate: 19.7% by weight with respect to the weight of the anhydrous cartilage product;

Hyaluronic acid: 0.3% by weight with respect to the weight of the anhydrous cartilage product;

Growth factor TGF-$\beta$1: 53.0 pg for every 100 mg of anhydrous cartilage product;

Growth factor TGF-$\beta$3: 31.3 pg for every 100 mg of anhydrous cartilage product;

Ash: 8.9% by weight with respect to the weight of the anhydrous cartilage product;

Calcium: 0.4% by weight with respect to the weight of the anhydrous cartilage product;

Phosphates: 0.3% by weight with respect to the weight of the anhydrous cartilage product.

Collagen hydrolysate with a degree of hydrolysis less than 3.0% is included in 77% of the protein hydrolysate.

The analytical characteristics of the cartilage product can slightly vary depending on the batch of cartilage product obtained.

Determination of the Degrees of Hydrolysis:

The degree of hydrolysis of the protein was determined by means of a standard method. It was expressed as the percentage of free amino acids in relation to total amino acids.

The degree of hydrolysis of the collagen hydrolysate was determined by means of a standard method. It was expressed as the percentage of free hydroxyproline in relation to total hydroxyproline.

Determination of the Growth Factors:

The following of ELISA kits (R&D Systems) were used following the protocols recommended by the manufacturer to determine the growth factors:

Quantikine porcine TGF-$\beta$1 (catalog: MB100B);

DuoSet Human TGF-$\beta$3 (catalog: DY243).

Example 2

Tablets of Porcine Tracheal Cartilage Product, Calcium Salt and Vitamin D3

The tablets were prepared following conventional methods.

Per Tablet:

| | |
|---|---|
| Porcine tracheal cartilage product | 300 mg |
| Hydroxyapatite | 400 mg |
| Vitamin D3 | 100 IU |

Example 3

Tablets of Porcine Tracheal Cartilage Product, Calcium Salt, Vitamin D3 and Vitamin K2

Per Tablet:

| | |
|---|---|
| Porcine tracheal cartilage product | 300 mg |
| Hydroxyapatite | 400 mg |
| Vitamin D3 | 100 IU |
| Vitamin K2 | 22.5 µg |

Biology

Example 4

Activity Stimulating Fibroblast Proliferation

The wound healing process is a highly ordered and controlled process characterized by different phases: inflammation, proliferation and remodeling (R. F. Diegelmann and M. C. Evans, *Front. Biosci.* 9, 283-289 (2004)). The healing process requires the coordination of several cells, growth factors and cytokines. Inflammation is the initial phase. In the wound healing process, fibroblast proliferation is involved in restoring structure and function in the wound (R. A. Clark, *Ann. N.Y. Acad. Sci.* 936, 355-367 (2001)).

Stimulation of the degree of fibroblast proliferation is also interesting as an anti-age treatment. The number of dermal fibroblasts decreases with aging and, therefore, there is a progressive loss of dermal tissue.

Materials and Methods

The degree of proliferation was quantified by measuring the incorporation of bromodeoxyuridine (BrdU) into DNA of proliferating cells during the replication phase. A specific anti-BrdU antibody colorimetric immunoassay, ELISA (Enzyme Linked Immunoadsorbent Assay) detection and subsequent reading of absorbance at 450 nm were used to quantify the incorporated BrdU. The amount of BrdU detected is proportional to the number of cells that have been divided and, therefore, proportional to the growth or proliferation experienced by the culture.

Human dermal fibroblasts were seeded at 5,000 cells/well in 96-well plates and after 24 hours, they were left over night with growth factor-deprived culture medium. The next day, the cells were treated at three concentrations (2 mg/ml, 500 µg/ml and 50 µg/ml) of a cartilage product of the present invention, specifically of the cartilage product of Example 1. The amount of bromodeoxyuridine was determined by means of specific immunoassay (technique ELISA) after 48 hours of exposure of the culture to the cartilage product.

A fibroblast culture with culture medium was used as a baseline control and the fibroblasts were exposed to 10% FCS (Fetal Calf Serum) culture medium as a positive control.

Results

As can be observed in FIG. 1, the cartilage product at the doses of 500 μg/ml and 2 mg/ml showed a statistically significant stimulating effect (p<0.05) on fibroblast proliferation when compared with the baseline control. Specifically, proliferation increased at the intermediate dose by 35.9% and by 73% at the high dose.

Example 5

Assessment of In Vitro Cell Migration Capacity

This study allows evaluating the induction capacity of cell migration in primary human dermal fibroblast culture, and it is therefore useful to evaluate the potential efficacy of a product in wound healing and as an anti-age treatment. In fact, with aging there is a decrease in the degree of fibroblast proliferation and migration.

Materials and Methods

The Oris™ Cell Migration assay system by Platypus was used to evaluate the potential effect of a cartilage product of the present invention on cell migration. This system consists of a special plate which allows seeding fibroblasts and their single-layer growth, but leaving a central area of the well cell-free as a result of the so-called Oris™ Cell Seeding Stoppers which restrict seeding to the outer annular region of the well. The Oris™ Cell Seeding Stoppers are subsequently removed and this area is subsequently occupied by cells during the migration process.

The human dermal fibroblasts were incubated for 48 hours in the presence of a cartilage product of the present invention, specifically of the cartilage product of Example 1 (2 mg/ml and 500 μg/ml), and they were then labeled with fluorescent calcein dye. The fluorescence emitted by the migrating cells was measured by means of a fluorometer. Photographs were also taken by fluorescence microscopy which allowed seeing the occupied area compared with the baseline control.

Culture medium was used as the baseline control and as positive controls were included 10% FCS (Fetal Calf Serum) culture medium and also culture medium with 5 ng EGF (Epidermal Growth Factor).

Results

Figure 2:
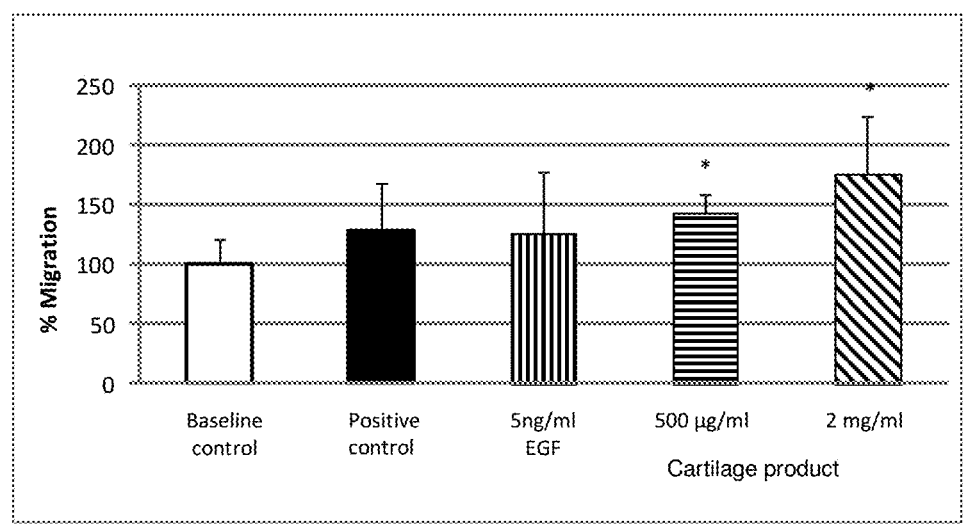
FIG. 2 shows the effect of the cartilage product on the percentage of human dermal fibroblast migration at 48 hours at three concentrations (250 µg/ml, 500 µg/ml and 2 mg/ml). The baseline control (human dermal fibroblast culture in culture medium and in the absence of the cartilage product) and two positive controls (a human dermal fibroblast culture in 10% FCS culture medium and in the absence of the cartilage product and a human dermal fibroblast culture in the absence of the cartilage product and in the presence of EGF) are also included.

As can be seen in FIG. 2, the cartilage product produced an important inductive effect on cell migration at 48 h of exposure for the concentrations of 500 μg/ml and 2 mg/ml (42% and 75% induction, respectively). It must further be pointed out that the effect of said product exceeded that shown the positive controls (10% FCS medium and EGF at 5 ng/ml).

Example 6

Assessment of the Moisturizing Action

Hyaluronic acid is an essential component health skin and is involved in hemostasis, moisturizing and repair processes. As a result of its capacity to retain water in a thousand-fold percentage equivalent, it carries out a primordial function in the skin. Young skin is rich in hyaluronic acid, however as one ages, the distribution and function of hyaluronic acid in the skin gradually change and the characteristics signs of aging such as wrinkles and expression lines appear.

Materials and Methods

To evaluate the inductive efficacy of skin moisturizing by a cartilage product of the present invention, specifically by the cartilage product of Example 1, a study was performed to quantify glycosaminoglycans, mainly hyaluronic acid synthesized by human dermal fibroblasts after incubation with the cartilage product (2 mg/ml, 500 μg/ml and 250 μg/ml) for 24 hours. To that end, the method of incorporating $^3$H-glucosamine into newly-synthesized glycosaminoglycans was used.

The bound radioactivity was analyzed in a liquid scintillation counter. The CPM (counts per minute) values obtained are proportional to the amount of hyaluronic acid synthesized in 90%.

The fibroblasts were exposed to TGF-β1 (transforming growth factor beta 1), known as an extracellular matrix protein production inducer, as the positive control. The baseline control consisted only of fibroblasts in culture medium.

Results

The cartilage product showed a mild moisturizing effect at 24 hours of exposure to the concentration of 500 μg/ml. Specifically, it stimulated hyaluronic acid synthesis by 12% when compared with the baseline control.

Example 7

Assessment of the Inductive Capacity of Elastin Production

In human skin, intrinsic aging is characterized by atrophy of the dermis due to collagen loss, degeneration of the elastin fiber network and loss of moisturize. Elastin is the protein conferring elastic properties to the skin.

Materials and Methods

The inductive capacity of skin elasticity by a cartilage product of the present invention, specifically of the cartilage product of Example 1, was evaluated from the quantification of elastin production in fibroblasts.

Human dermal fibroblasts were seeded in 96-well culture plates and were kept growing until reaching confluence. Then they were exposed for 72 hours to concentrations of 2 mg/ml, 500 μg/ml and 250 μg/ml. After this treatment period ended, the cells were washed and fixed for ELISA processing. A primary anti-elastin antibody (Monoclonal Anti-Elastin antibody produced in mouse, Sigma), followed by a secondary antibody conjugated to the horseradish peroxidase (HRP) enzyme and developed with o-phenylenediamine (HRP substrate) and urea-$H_2O_2$, were used in this process. Absorbance was read in an ELISA reader at 492 nm.

The value of elastin produced was pondered with that of total protein in each experimental condition, resulting in the values of the elastin/total protein production index.

The fibroblasts were exposed to TGF-β1 (transforming growth factor beta 1) as the positive control. The fibroblasts were cultured in culture medium as the baseline control.

Results

Figure 3:
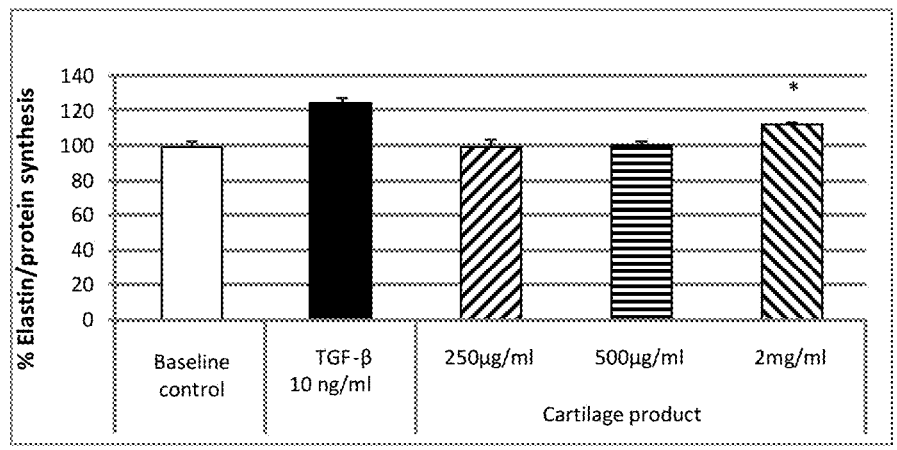
FIG. 3 shows the effect of the cartilage product on the elastin synthesis percentage in a human dermal fibroblast culture at 72 hours of exposure at three concentrations (250 µg/ml, 500 µg/ml and 2 mg/ml). The baseline control (human dermal fibroblast culture in culture medium and in the absence of the cartilage product) and the positive control (human dermal fibroblast culture in the absence of the cartilage product and in the presence of TGF-β) are also included.
Figure 4:
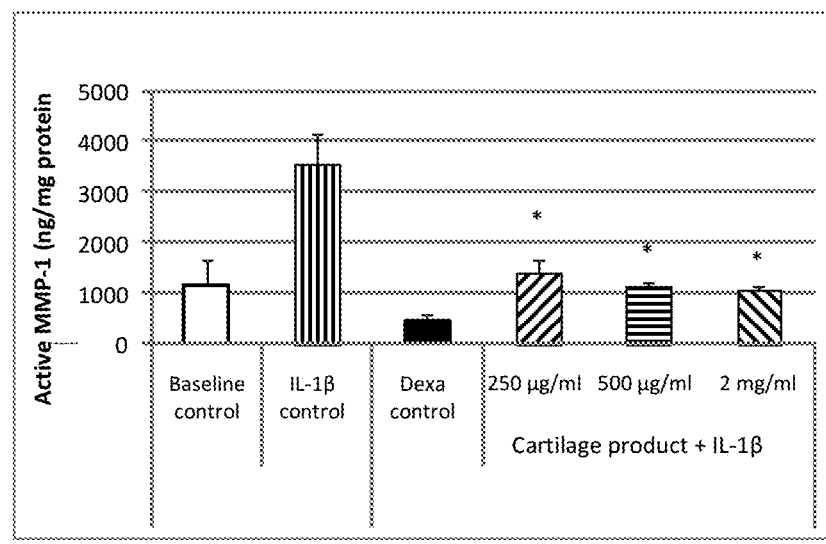
FIG. 4 shows the effect of the cartilage product on metalloprotease 1 (MMP-1) activity in an IL-1β-stimulated human dermal fibroblast culture at three concentrations (250 µg/ml, 500 µg/ml and 2 mg/ml). The baseline control (human dermal fibroblast culture in culture medium and in the absence of the cartilage product and of IL-1β), the IL-1β-stimulated control and the positive inhibition control (human dermal fibroblast culture in the absence of the cartilage product and in the presence of IL-1β and of dexamethasone) are also included.

As it can be seen in FIG. 3, the cartilage product showed an important inductive effect on elastin production at the highest concentration studied (2 mg/ml). It should be mentioned that close to 50% of the value shown by the TGF-β control, a potent inductor of elastin and extracellular matrix protein synthesis, was achieved.

Example 8

Determination of the Inhibitor Potential of MMP-1 Activity

There is a loss of extracellular matrix, an increase in metalloproteases (MMPs) degrading collagen type I responsible for firmness of the skin, as well as a loss of fibroblasts and of the vascular network with aging. It is estimated that collagen of the dermis decreases 1% per year over the adult lifetime and as age increases, metalloprotease levels also increase, which progressively increases the loss of collagen. The presence of high levels of some metalloproteases has been associated with cell destruction in a wide variety of pathological and aging processes (K. C. N. Chang et al., *Mol. Endocrinol.* 22(11), 2407-2419 (2008); G. J. Fisher et al., *Am. J. Pathol.* 174(1), 101-114 (2009); A. L. Clutterbuck et al., *Curr. Drug Targets* 10(2), 1245-1254 (2009); H. Nagase et al., *Cardiovascular Research* 69, 562-573 (2006))

Materials and Methods

To evaluate the effect of a cartilage product of the present invention, specifically of the cartilage product of Example 1, on metalloprotease regulation, MMP-1 activity in a primary human dermal fibroblast culture exposed to the cartilage product and induced with IL1-β during 48 hours was determined.

Human dermal fibroblasts were seeded in 24-well culture plates. After reaching confluence and deprivation serum-free medium for 16 hours, the cartilage product was applied (2 mg/ml, 500 µg/ml and 250 µg/ml). After 24 hours, IL-1β was applied as a stimulator of MMP production and the culture was maintained for another 24 hours. At the end of treatment, the supernatant was pooled and the active metalloprotease was quantified by means of a specific immunofluorometric assay after enzyme activation with APMA (p-AminoPhenylMercuric Acetate).

The values of active MMP-1 were weighted by the values of total protein, previously determined by the method of bicinchoninic acid, BCA (Pierce BCA Protein Assay Kit).

The baseline control consisted of culture medium. An IL-1β-stimulated control group was also included in the study. Dexamethasone at 5 µM (dexa control), a strong anti-inflammatory glucocorticoid, was used as the positive inhibition control.

Results

The cartilage product showed a strong inhibitory effect (p<0.05) on IL-1β-induced metalloprotease 1 activity at all the studied doses and in a dose-dependent manner, with a reduction of 61%-70% with respect to the IL-1β-stimulated control.

Example 9

Efficacy of the Porcine Tracheal Cartilage Product in the Healing Quality of Wounds Materials and Methods The study was performed in an excision wound model a Yucatan-type miniature pig. The wounds were full-thickness with a diameter of 3 cm. Two female pigs were used in the study and eight wounds were made per animal. Four wounds were treated with the cartilage product of Example 1 and the other four were not treated and were considered the control group. The product was applied daily for 14 days in the form of a gel formed by 1 g of cartilage product resuspended in 1 ml of sterile saline. Healing was monitored visually with photographs and granulation, epithelialization, moisturizing and general observations for each wound were evaluated on days 1, 2, 4, 8 and 15.

Results

The visual evaluation demonstrated that wounds treated with the cartilage product of the present invention presented less hypertrophic scarring than those corresponding to the non-treated control.

Example 10

Effect of the Porcine Tracheal Cartilage Product on Muscular Atrophy

Measurement of the size of myotubes is a suitable approach for studying compounds that can prevent or treat skeletal muscle atrophy or induce hypertrophy. The C2Cl2 cell line has been widely used as an in vitro model for muscle atrophy and hypertrophy studies. C2Cl2 cells proliferating in the form of mononucleated myoblasts which subsequently fused to and differentiated into polynucleated myotubes.

Materials and Methods

C2Cl2 myoblasts were seeded in culture plates with growth medium (DMEM/10%, fetal bovine serum, 2 mM L-glutamine) and were left to grow to confluence. The cells were then treated with a medium (MEM/2% bovine serum, 2 mM L-glutamine) to induce differentiation of myoblasts into myotubes. After 5 days, the myotubes were incubated for 48 hours with serum-free medium (DMEM/2 mM L-glutamine) with/without the cartilage product of Example 1 (0.3, 1 and 1.5 mg/ml). After treatment, the myotubes were fixed with formaldehyde and treated with a myosin heavy chain antibody. The size of the myotubes was determined by means of fluorescence microscopy.

Results

The elimination of the differentiation serum (0% control) resulted in an approximate reduction of 20% of the size of the myotubes compared with the myotubes that were maintained in differentiation conditions (2% control).

Treatment with the cartilage product of the present invention was capable of counteracting in a statistically significant manner (p<0.05) myotube atrophy at all the studied concentrations.

Example 11

Effect of the Cartilage Product in an In Vitro Model of Psoriasis

Release of IL-17 cytokine by $CD4^+T$ Lymphocytes Stimulated with a Mixture of Anti-CD3 and Anti-CD28 Antibodies Psoriasis is an immunological disease mediated by T lymphocytes which induce specific physiopathological responses in keratinocytes by means of the release of cytokines. Cytokines signal and induce the expression of specific genes and the development of the pathology. IL-17 is a crucial cytokine in psoriasis pathogenesis. In fact, drugs attacking said cytokine are effective in the treatment of this disease (A. M. Lin et al., *J. Immunol.* 187 (1), 490-500 (2011)). An active product for this disease could act both at the lymphocyte level (inhibiting the activation/infiltration or the release of cytokines) and at the keratinocyte level (inhibiting cytokine signaling).

Materials and Methods

The $CD4^+T$ cells were isolated and pre-incubated for 24 hours in culture medium with or without the cartilage product of Example 1 (0.25, 0.5, 1 mg/ml) or reference cyclosporin A. In parallel, the 96-well plate was covered with anti-CD3 antibody. The cells were transferred to the plate with culture medium with anti-CD28 antibody and with or without the cartilage product or the reference. A no-stimulated control was included, incubating the cells in wells not covered with antibody and with the absence of CD28 antibody. The cells were then incubated for 24 hours and the supernatants of the culture were pooled to quantify IL-17 levels by means of an ELISA assay (R&D Systems, ref. DY317).

Results

The activation of CD4+T cells with anti-CD3 and anti-CD28 antibodies resulted in a significant release of IL-17. The reference compound, cyclosporin A, inhibited the release of IL-17 by 100%.

The cartilage product of the present invention at 1 mg/ml inhibited IL-17 levels in a statistically significant manner: 42% inhibition.

Example 12

Effect of the Cartilage Product on an Animal Model of Osteoporosis and Osteoarthritis Materials and Methods A model of ovariectomy-induced osteoporosis and anterior cruciate ligament transection (ACLT)-induced osteoarthritis in rats was used.

The study included the following treatment groups:

Blank: Group without induction of osteoporosis or osteoarthritis. Treated with 1 ml of water.

Control 1: Group with induction of osteoporosis and osteoarthritis treated with 1 ml of water. It is the control group for treatment with the ossein-hydroxyapatite compound (OHC; see patent EP255565B1).

OHC compound: Reference product used at a dose of 290.5 mg/kg/day in rats.

Control 2: Group with induction of osteoporosis and osteoarthritis treated with 1 ml of water. It is the control group for treatment with the composition based on the cartilage product of the present invention.

Composition 1 at a low dose (composition 1 LD): Formulation consisting of 600 mg of the cartilage product of Example 1, 800 mg of hydroxyapatite and 200 IU of vitamin D3. The administered dose in rats was 163.5 mg/kg/day of this formulation.

Composition 2 at a high dose (composition 2 HD): Formulation consisting of 900 mg of the cartilage product of the Example 1, 1,200 mg of hydroxyapatite and 200 IU of vitamin D3. The administered dose in rats was 245 mg/kg/day of this formulation.

The amount of cartilage product and hydroxyapatite of compositions 1 and 2 used in the study was less than the amount of ossein and hydroxyapatite of the reference product (OHC compound).

The number of rats per treatment group was 15. The compounds were administered daily for 12 weeks by means of intragastric probe, resuspended in 1 ml of water.

Cartilage degradation was evaluated by means of the scale recommended by OARSI (K. P. H. Pritzker et al, *Osteoarthritis and Cartilage* 14, 13-29 (2006)). The effects on mineral density and on bone microarchitecture bone were evaluated by means of micro-CT technique (M. L. Bouxsein et al., *J. Bone Miner. Res.* 25 (7), 1468-86 (2010))

Figure 5:
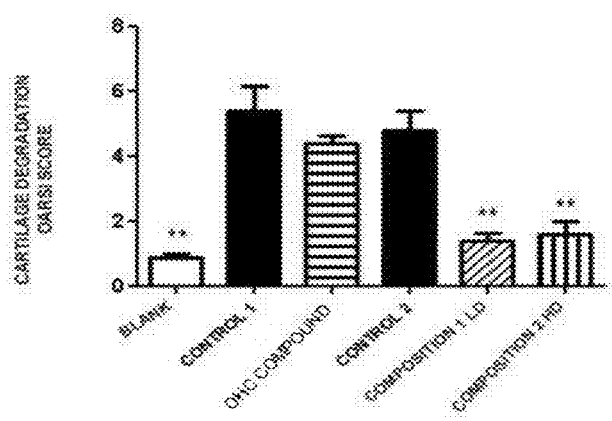
FIG. 5 shows the effect of two compositions based on cartilage product, hydroxyapatite and vitamin D3, on cartilage degradation at a low dose (composition 1 LD) and at a high dose (composition 2 HD), using the OARSI scoring system. are also included. The blank (group of rats without induction of osteoporosis or osteoarthritis), control 1 (group of rats with induction of osteoporosis and osteoarthritis; this was the control group for treatment with the reference compound), control 2 (group of rats with induction of osteoporosis and osteoarthritis; this was the control group for treatment with the cartilage product-based compositions) and the OHC compound (reference product) are also included.

Results in Osteoarthritis:

Treatments with composition 2 at a high dose and also with composition 1 at a low dose have shown to be highly effective in reducing cartilage degradation (p<0.05). The compound OHC showed no significant effect (see FIG. 5).

Figure 6:
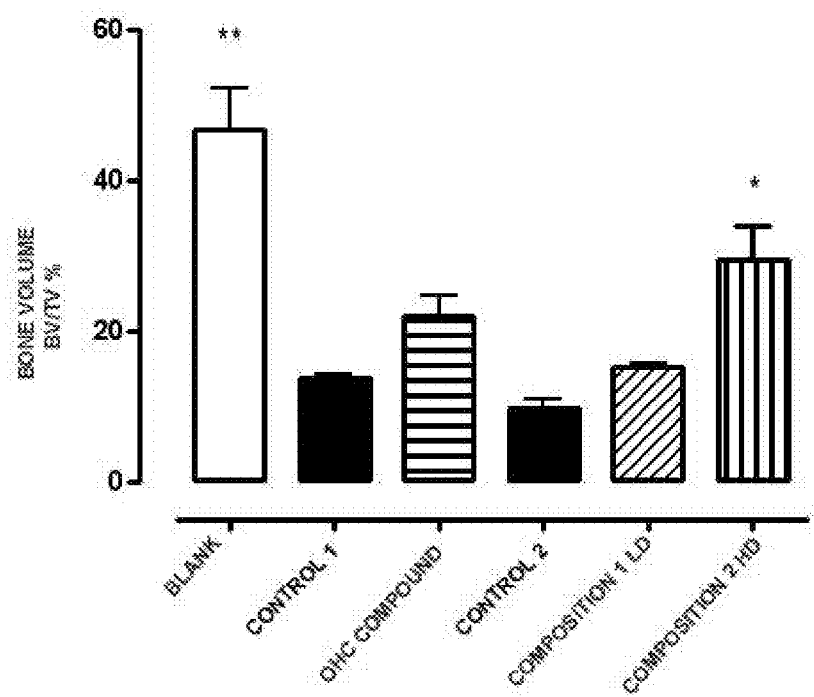
FIG. 6 shows the effect of two compositions based on cartilage product, hydroxyapatite and vitamin D3, on bone volume (BV/TV %) at a low dose (composition 1 LD) and at a high dose (composition 2 HD). The blank (group of rats without induction of osteoporosis or osteoarthritis), control 1 (group of rats with induction of osteoporosis and osteoarthritis; this was the control group for treatment with the reference compound), control 2 (group of rats with induction of osteoporosis and osteoarthritis; this was the control group for treatment with the cartilage product-based compositions) and the OHC compound (reference product) are also included.

Results in Osteoporosis:

As can be seen in FIG. 6, treatments with the OHC compound and composition 1 at a low dose caused a considerable increase in the bone volume percentage. Nevertheless, treatment with composition 2 at a high dose was the only treatment that entailed a statistically significant increase in bone volume percentage (p<0.05).

Figure 7:
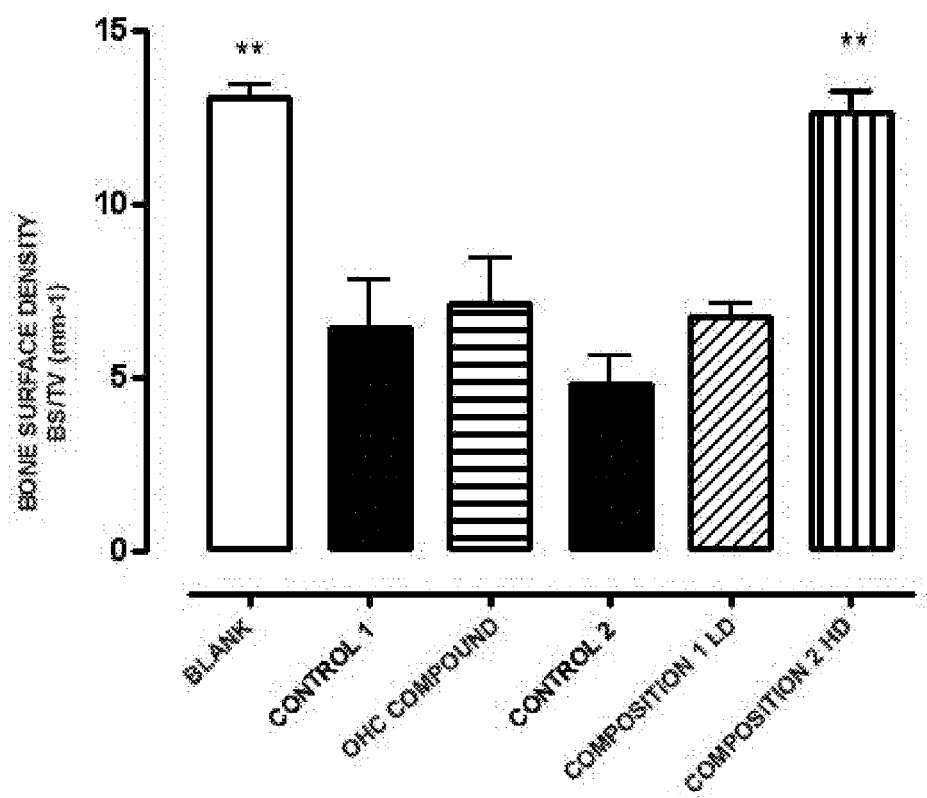
FIG. 7 shows the effect of two compositions based on cartilage product, hydroxyapatite and vitamin D3, on bone surface density (BS/TV ($mm^{-1}$)) at a low dose (composition 1 LD) and at a high dose (composition 2 HD). The blank (group of rats without induction of osteoporosis or osteoarthritis), control 1 (group of rats with induction of osteoporosis and osteoarthritis; this was the control group for treatment with the reference compound), control 2 (group of rats with induction of osteoporosis and osteoarthritis; this was the control group for treatment with the cartilage product-based compositions) and the OHC compound (reference product) are also included.

As can be seen in FIG. 7, treatment with the OHC compound caused only a mild effect on bone surface density (comparing the OHC compound with control 1). Treatments with composition 1 at a low dose and with composition 2 at a high dose caused a considerable increase in bone surface density, the effect of composition 2 at a high dose being statistically significant (p<0.01).

Figure 8:
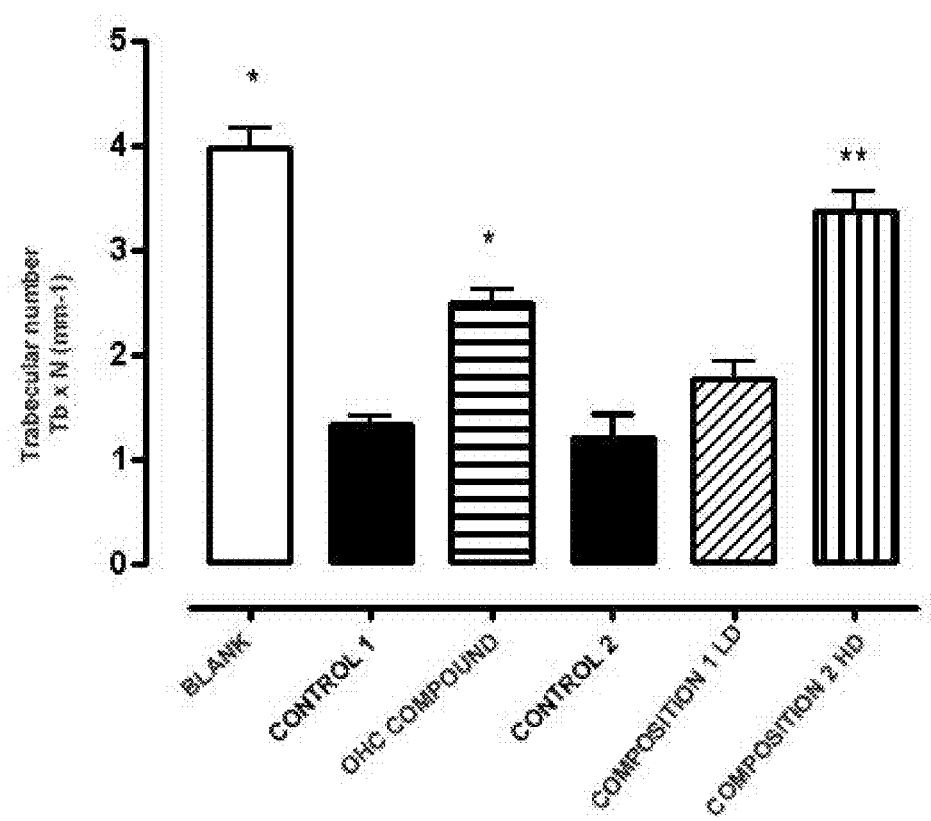
FIG. 8 shows the effect of two compositions based on cartilage product, hydroxyapatite and vitamin D3, on trabecular number (Tb×N ($mm^{-1}$)) at a low dose (composition 1 LD) and at a high dose (composition 2 HD). The blank (group of rats without induction of osteoporosis or osteoarthritis), control 1 (group of rats with induction of osteoporosis and osteoarthritis; this was the control group for treatment with the reference compound), control 2 (group of rats with induction of osteoporosis and osteoarthritis; this was the control group for treatment with the cartilage product-based compositions) and the OHC compound (reference product) are also included.

In addition, FIG. 8 shows that treatment with composition 1 at a low dose caused a non-statistically significant increase in the trabecular number (45% increase). The OHC compound caused an 88% increase which is, statistically significant (p<0.05). Composition 2 at a high dose was the treatment that showed better results, with an increase in the trabecular number of 180% (p<0.01).

The invention claimed is:

1. A cartilage product, comprising:
   a) between 67% and 87% by weight of protein hydrolysate with a degree of hydrolysis comprised between 0.5% and 3.0%, with respect to the weight of the anhydrous cartilage product;
   b) between 15% and 25% by weight of chondroitin sulfate, with respect to the weight of the anhydrous cartilage product;
   c) between 0.1% and 1.0% by weight of hyaluronic acid, with respect to the weight of the anhydrous cartilage product;
   d) between 20 pg and 200 pg of TGF-β1 for every 100 mg of anhydrous cartilage product, and
   e) between 20 pg and 200 pg of TGF-β3 for every 100 mg of anhydrous cartilage product.

2. The cartilage product of claim 1 which is an aqueous solution.

3. The cartilage product of claim 1 which is a solid product.

4. The cartilage product of claim 1, comprising:
   a) 77% by weight of protein hydrolysate with a degree of hydrolysis of the 1.7%, with respect to the weight of the anhydrous cartilage product;
   b) 19.7% by weight of chondroitin sulfate, with respect to the weight of the anhydrous cartilage product;
   c) 0.3% by weight of hyaluronic acid, with respect to the weight of the anhydrous cartilage product;
   d) 53.0 pg of TGF-β1 for every 100 mg of anhydrous cartilage product, and
   e) 31.3 pg of TGF-β3 for every 100 mg of anhydrous cartilage product.

5. The cartilage product of claim 1, wherein the protein hydrolysate includes collagen hydrolysate and the collagen hydrolysate comprises between 45% and 65% by weight of the collagen hydrolysate with a degree of hydrolysis less than 3.0%, with respect to the weight of the anhydrous cartilage product.

6. The cartilage product of claim 5, comprising 54.9% by weight of collagen hydrolysate with a degree of hydrolysis less than 3.0%, with respect to the weight of the anhydrous cartilage product.

7. The cartilage product of claim 5, wherein the collagen hydrolysate has a degree of hydrolysis of 0.1%.

8. A cartilage product, characterized by the following analytical parameters:
   Degree of hydrolysis of the protein: comprised between 0.5% and 3.0%;
   Degree of hydrolysis of the collagen hydrolysate: less than 3%;

Protein hydrolysate: between 67% and 87% by weight with respect to the weight of the anhydrous cartilage product wherein the protein hydrolysate includes collagen hydrolysate;

Collagen hydrolysate: between 45% and 65% by weight with respect to the weight of the anhydrous cartilage product;

Chondroitin sulfate: between 15% and 25% by weight with respect to the weight of the anhydrous cartilage product;

Hyaluronic acid: between 0.1% and 1.0% by weight with respect to the weight of the anhydrous cartilage product;

Growth factor TGF-β1: between 20 pg and 200 pg for every 100 mg of anhydrous cartilage product;

Growth factor TGF-β3: between 20 pg and 200 pg for every 100 mg of anhydrous cartilage product.

9. A food supplement or a functional food comprising the cartilage product according to claim 1 and at least one nutritional excipient.

10. A cosmetic composition comprising the cartilage product according to claim 1 and at least one cosmetically acceptable excipient.

11. A pharmaceutical composition comprising the cartilage product according to claim 1 and at least one pharmaceutically acceptable excipient.

12. A food supplement or a functional food comprising the cartilage product according to claim 8 and at least one nutritional excipient.

13. A cosmetic composition comprising the cartilage product according to claim 8 and at least one cosmetically acceptable excipient.

14. A pharmaceutical composition comprising the cartilage product according to claim 8 and at least one pharmaceutically acceptable excipient.

* * * * *